(12) United States Patent
Kallenbach et al.

(10) Patent No.: US 10,449,278 B2
(45) Date of Patent: Oct. 22, 2019

(54) HEART PUMP DEVICE AND METHOD FOR OPERATING SAME

(71) Applicant: Berlin Heart GmbH, Berlin (DE)

(72) Inventors: Sebastian Kallenbach, Kassel (DE); Helge Krambeck, Berlin (DE); Ralph Breuel, Schwerin (DE)

(73) Assignee: BERLIN HEART GMBH, Berlin (DE)

( * ) Notice: Subject to any disclaimer, the term of this patent is extended or adjusted under 35 U.S.C. 154(b) by 0 days.

(21) Appl. No.: 15/558,961

(22) PCT Filed: Mar. 17, 2016

(86) PCT No.: PCT/EP2016/055810
§ 371 (c)(1),
(2) Date: Sep. 15, 2017

(87) PCT Pub. No.: WO2016/146748
PCT Pub. Date: Sep. 22, 2016

(65) Prior Publication Data
US 2018/0243490 A1    Aug. 30, 2018

(30) Foreign Application Priority Data
Mar. 17, 2015   (EP) .................................... 15159496

(51) Int. Cl.
*A61M 1/10*   (2006.01)
*A61M 1/12*   (2006.01)

(52) U.S. Cl.
CPC ........ *A61M 1/1086* (2013.01); *A61M 1/1015* (2014.02); *A61M 1/1036* (2014.02);
(Continued)

(58) Field of Classification Search
CPC .............. A61M 1/1086; A61M 1/1036; A61M 1/1015; A61M 1/127; A61M 1/122;
(Continued)

(56) References Cited

U.S. PATENT DOCUMENTS

| 2011/0178361 A1* | 7/2011 | Yomtov | ................. | A61M 1/10 600/16 |
| 2013/0183176 A1* | 7/2013 | Wampler | ............ | F04D 29/0413 417/420 |

(Continued)

FOREIGN PATENT DOCUMENTS

| DE | 10 2013 013700 A1 | 10/2014 |
| WO | WO 2012/012552 A1 | 1/2012 |

OTHER PUBLICATIONS

International Search Report with English translation, dated Jun. 2, 2016, pp. 1-5, Issued in International Application No. PCT/EP2016/055810, European Patent Office, Rijswijk, Netherlands.

*Primary Examiner* — Rex R Holmes
(74) *Attorney, Agent, or Firm* — Brinks Gilson & Lione

(57) ABSTRACT

A heart pump device may be provided with an implantable heart pump, which has at least one sensor, wherein at least one of the sensors is a sensor for a rotor of the heart pump, and with a control device, which is connected to the heart pump by means of a transcutaneous line, characterized by a signal processing device, which on the one hand is connected by means of the transcutaneous line to the control device, and which on the other hand is connected to at least one sensor of the heart pump and transmits signals of at least one sensor via the transcutaneous line to the control unit. The signal processing device may be for a pre-processing of the sensor data for more efficient transmission via the transcutaneous line.

13 Claims, 3 Drawing Sheets

(52) U.S. Cl.
CPC ............ *A61M 1/122* (2014.02); *A61M 1/127* (2013.01); *A61M 1/101* (2013.01); *A61M 1/1031* (2014.02); *A61M 1/12* (2013.01); *A61M 2205/33* (2013.01); *A61M 2205/3303* (2013.01); *A61M 2205/3334* (2013.01); *A61M 2205/3365* (2013.01); *A61M 2205/3523* (2013.01); *A61M 2205/8243* (2013.01); *A61M 2230/205* (2013.01); *A61M 2230/30* (2013.01); *A61M 2230/50* (2013.01); *A61M 2230/62* (2013.01); *A61M 2230/63* (2013.01)

(58) Field of Classification Search
CPC ...... A61M 2230/50; A61M 2205/3523; A61M 2205/3334; A61M 2205/3365; A61M 2230/205; A61M 2230/30; A61M 2230/63; A61M 2230/62; A61M 2205/33; A61M 2205/3303; A61M 1/12; A61M 1/101; A61M 2205/8243; A61M 1/1031
See application file for complete search history.

(56) References Cited

U.S. PATENT DOCUMENTS

| | | | |
|---|---|---|---|
| 2014/0066691 A1* | 3/2014 | Siebenhaar | A61M 1/12 |
| | | | 600/16 |
| 2014/0303426 A1 | 10/2014 | Kerkhoffs et al. | |
| 2015/0367049 A1* | 12/2015 | Chen | A61M 1/122 |
| | | | 600/16 |

* cited by examiner

HEART PUMP DEVICE AND METHOD FOR OPERATING SAME

CROSS-REFERENCE TO RELATED APPLICATIONS

This application is a 371 nationalization of international patent application PCT/EP2016/055810 filed date of Mar. 17, 2016, the entire contents of which are hereby incorporated by reference, which in turn claims priority under 35 USC § 119 to European patent application EP 15159496.7 filed on Mar. 17, 2015.

TECHNICAL FIELD

The invention lies in the field of electrical engineering and especially medical engineering and can be used specifically in conjunction with heart pumps.

DETAILED DESCRIPTION

Figure 1:
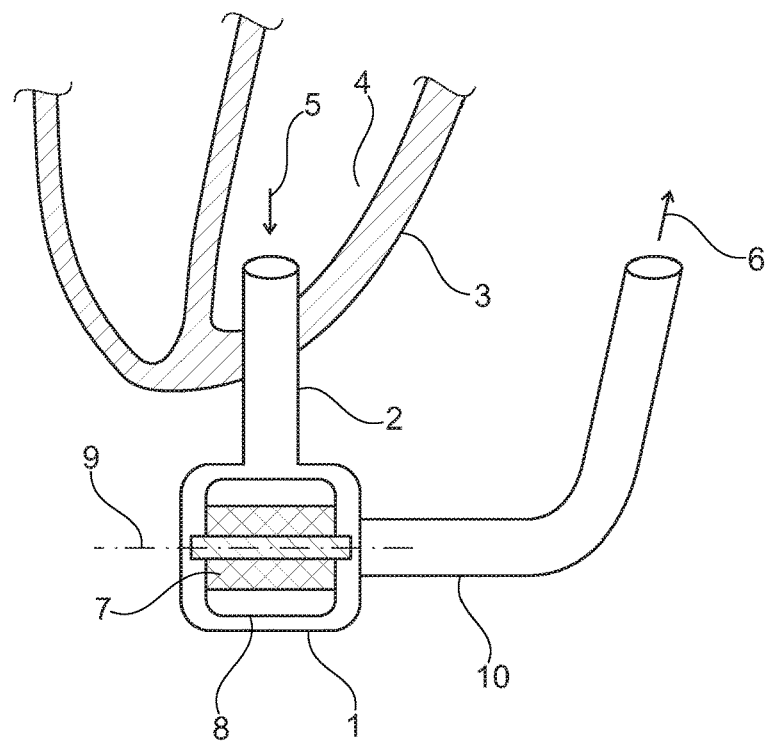
FIG. 1 shows a section through a heart wall with an implanted heart pump of a first design.

For some time, implantable electric heart pumps for assisting the human heart have been known, which for example can be designed as an LVAD (left ventricular assist device), RVAD (right ventricular assist device) or BiVAD (bi-ventricular assist device) and in this case convey blood from the left heart ventricle into the aorta. Pumps of this type are usually supplied with power and controlled from outside the body. To this end, one or more wired lines is/are usually provided, which supply electrical power to, and control, the actual heart pump, in particular a motor provided in the heart pump. In addition, data is detected within the implanted heart pump via sensors, such as the rotor position of the heart pump, the pump temperature, the ventricle blood pressure, the blood temperature, position information, angular accelerations, acoustic signals, intrathoracic pressure, and similar variables, and this data is received and processed, in particular also stored, by a control device disposed outside the patient's body.

A number of lines or cores of lines are usually provided for connection of the sensors and of the pump motor to the control device so as to transport all data and the energy in the form of an individual wiring through a combined transcutaneous or percutaneous cable. Due to the large number of cores, the cross-section of the transcutaneous lines or of the cable is relatively large, so that the primary piercing point poses an increased infection risk. In addition, a combined line of this type is rigid due to the large cross-section and is likely to break. The number of sensors is hereby limited, since the diameter of the combined line increases further due to further lines that need to be added.

Solutions are also known in which a transmission of data takes place via a radio link from inside the body to outside the body, however a communication connection of this type has certain failure risks, so that a wired connection is desirable as safeguard. By way of example, a continuously determined rotor position of the drive of the heart pump can be important for the drive control.

Against the background of the prior art, the object of the present invention is therefore to connect a control device—arranged outside the body—for a heart pump device to a heart pump with minimal effort and minimised risk of infection.

The invention thus relates to a heart pump device with an implantable heart pump that has at least one sensor, wherein at least one of the sensors is one of the following sensors: a position sensor for a rotor of the heart pump; a position and/or acceleration sensor; a volume flow rate sensor; a temperature sensor; a pressure sensor; a pressure difference sensor; an oxygen saturation sensor; a chemical sensor for blood analysis. The heart pump device also comprises a control device that is connected to the heart pump by means of a transcutaneous or percutaneous line. By way of example, a transcutaneous line is understood to mean a line that is guided through the skin. By contrast, a percutaneous line by way of example runs entirely in the body and is often guided at least to a point in the vicinity of the skin surface and for example is coupled to a TET (transcutaneous energy transfer) system. Here, the TET system is configured in such a way that, besides energy, preferably digital data can also be exchanged.

The invention also relates to a signal processing device, which on the one hand is connected by means of the transcutaneous or percutaneous line to the control device and which on the other hand is connected to at least one sensor of the heart pump and in a first operating state transmits signals of the at least one sensor to the control unit. Here, the signals are transmitted in some embodiments via the transcutaneous or percutaneous line.

The signal processing device, similarly to the heart pump, is implantable and is directly connected to one or more sensors of the heart pump and provides a pre-processing of the signals from one or more sensors in such a way that these signals by way of example can be transmitted in a simplified manner via the transcutaneous or percutaneous line. Here, signals from different sensors can also be combined or connected, for example by combining a number of signals via a bus system. In particular, the signal processing device in a first operating state of the heart pump device can combine a multiplicity of signals to be transmitted—or in some exemplary embodiments all signals to be transmitted—from sensors and can transmit these via a transcutaneous or percutaneous line embodied as a databus. The transcutaneous line for this purpose can have one or more cores of electrical conductors and can serve as a line for a serial or parallel bus. Transmission via an optical signal line by the signal processing device is also possible. In addition, a combination of the energy-transmitting lines with the data-transmitting lines is possible (power-line communication).

In order to set up a databus system, fewer lines are usually required than in the case of an individual wiring of the sensors and individual connection of the sensors to the control device arranged outside the patient's body.

In addition, the signal processing device can store data of the individual sensors and for example can also store data suitable for a calibration of the signals. This has the advantage that the data can be interpreted in the control device independently of the further communication path over which it must travel between the signal processing device and the control device. The information arriving at the control device is not dependent on the individual pairing between a heart pump and a control device. In the event of a replacement of the control device, there is thus no need for any calibration or initialisation with a specific heart pump. This leads to significant simplifications with regard to the storage and installation of control devices. There is also no need to set up and use a heart pump and control device as a fixed pair in each individual case.

The signal processing device is connected in some exemplary embodiments at least to one of the aforementioned sensors. In one embodiment, at least one of the sensors is a position sensor of a rotor of the heart pump. In this case, the position sensor is for example a sensor that gives the position of the rotating rotor of an electric motor in the heart pump. The transmission of position data of this type is important for the control in particular of brushless electric motors, which are used advantageously in the field of medical engineering, since they are extremely efficient, can be easily controlled, and are low-maintenance.

A sensor that determines the angular position of the rotor by calculating current and voltage of a brushless electric motor via the rotor retroactivity can also serve as sensor for the position of the rotor of the heart pump.

The signal processing device can additionally also be connected to further sensors, for example two, three, four or more sensors, wherein these sensors can be provided in or on the heart pump and for example are formed as one of the aforementioned sensors or as pump temperature sensor, blood pressure sensor or blood temperature sensor. The signal processing device and the implantable heart pump can undergo an initial set-up together with the used sensors at the time of initial operation or at the factory prior to initial operation, wherein calibration occurs via known reference values and corresponding calibration parameters can be stored in the signal processing device. The heart pump can thus cooperate, jointly with the signal processing device, with any external control device without further calibration. The external control device therefore can be replaced without difficulty and can be used without further initial set-up.

The signal processing device is advantageously arranged directly on the heart pump. This allows a problem-free joint implantation of heart pump and signal processing device and additionally short signal paths between the sensors of the heart pump and the signal processing device. The signal processing device can also be held mechanically on the heart pump, for example can be mounted thereon, so that hereby the relative position of heart pump and signal processing device is clearly defined.

A further advantageous embodiment of the invention provides that a transmitting device is provided in the immediate vicinity of the heart pump, in particular is directly connected thereto, and processes the signals of at least one sensor and transmits these by means of a wireless connection. For the normal situation of fault-free operation, the data detected by the sensors can be transmitted via radio without use of the transcutaneous line. However, it is conceivable to use both transmission paths in parallel and to compare the transmitted signals in the control device so as to achieve a higher reliability. At least in the case in which the transmitting device fails, a switch is made immediately to the signal processing device and transmission via the transcutaneous line. In addition, the transcutaneous or percutaneous line is required permanently for the transmission of electrical energy in the form of a feed voltage for a motor of the heart pump.

A further advantageous embodiment of the invention provides that a switching module is provided within the signal processing device, which switching module causes a second operating state to be implemented in the event of a fault of the signal processing device, in which second operating state the signal of the position sensor (or of the particular sensor used) is transmitted directly via the transcutaneous or percutaneous line, with bypassing of key parts of the signal processing device.

If, by way of example, a position sensor is used for a rotor of a heart pump and the data detected by means of this position sensor is processed in the first operating state of the heart pump device by means of the signal processing device and is transmitted via the transcutaneous or percutaneous line, the signals in the second operating state are substantially not processed by the signal processing device, but instead are fed directly into the transcutaneous or percutaneous line. Since a continuous and reliable transmission of the axial position of the rotor and/or the angular position of the motor of the heart pump can be very important for the operation and the control of the motor depending on the pump type used, these variables of the corresponding sensor have to be transmitted with increased certainty. For this reason, the signal processing device can have a self-monitoring device, for example what is known as a watchdog, which detects malfunctions and in the event of a malfunction, by means of the switching module, bypasses the signal path connecting the corresponding sensor, in particular the position sensor, to the signal processing device and further to the control device, in such a way that the signal of the sensor is guided past key parts of the signal processing device and is guided directly via the transcutaneous or percutaneous line to the control device.

It can also be provided that further sensors are qualified in such a way that in the case of a malfunction of the signal processing device the signals delivered thereby are conducted directly by a switching module and are conducted past key parts of the signal processing device, via the transcutaneous or percutaneous line to the control device. However, in this case, since the transcutaneous line manages with minimal cores, the transmission of all sensor signals directly via the transcutaneous line is not necessarily possible. However, the transmission of the most important signals via the transcutaneous or percutaneous line in the second operating state is also secure if the signal processing device fails, for example.

For an advantageous embodiment of the invention, it can additionally be provided for example that the signal processing device has at least one memory device for storing system parameters, in particular parameters of the heart pump, and/or measured values of one or more sensors. A memory device of this type allows the calibration of the pairing of heart pump and signal processing device and also the storage of critical sensor data, wherein alarm signals for example are to be output when said critical sensor data occur or are overshot.

The signal processing device advantageously has a microcontroller and/or a transceiver, for example an RS485 transceiver. The heart pump device is thus equipped for efficient data transmission by means of communication standards which are only susceptible to faults to a minimal extent.

A further advantageous embodiment of the invention provides that the signal processing device has at least one flexible, in particular bendable or foldable printed circuit board. The signal processing device is usually constructed as an electric circuit with individual circuit elements and/or integrated circuits, for example also ASICs. On account of the small amount of space available, flexible or foldable printed circuit boards which can be adapted accordingly to the amount of space available are suitable for the construction.

In this regard, it can be provided particularly advantageously that the signal processing device is arranged annularly around an inflow or outflow channel of the heart pump. In the form of a bendable printed circuit board, the signal processing device can form an annular polygon, which surrounds an inflow or outflow line of the pump.

It can also be provided that the signal processing device is arranged on a flat housing base of the heart pump. A printed circuit board of the signal processing device can thus form a housing base of the pump or can run parallel to a housing base of the pump.

Apart from a heart pump device, the present invention also relates to a method for operating a heart pump device in one of the above-described embodiments, in which the heart pump together with its signal processing device is connected to a control device, and in which pump parameters are detected and are stored in the signal processing device. As a result, the pump is set up initially with the signal processing device and is calibrated as appropriate, and therefore the heart pump works together with any control device without the need for a further adaptation. The necessary calibration parameters are stored in the memory device of the signal processing device and can be called up therefrom.

During operation, the signal processing device forwards pre-processed signals from sensors via a databus by means of the transcutaneous or percutaneous line.

The invention will be presented hereinafter with reference to an exemplary embodiment in figures of a drawing and will be described hereinafter.

FIG. 1 shows an implantable heart pump 1, the inlet connection piece 2 of which is embedded in a heart wall 3 in the region of the left ventricle, in such a way that the pump 1 can convey blood from the heart chamber 4 into an artery (not illustrated). The direction of flow of the blood is indicated by the arrows 5, 6. The heart pump 1 has a rotor 7, which on the 1 hand has electromagnetic drive elements, such as an armature, and on the other hand conveying elements 8 in the form of blades, which for example convey blood in the axial direction 9 to the pump outlet 10. Sensors for various physiological variables, such as blood temperature and ventricle pressure, are usually arranged in the region of the heart pump 1, and also sensors for measuring the temperature of elements of the pump, a sensor for the acceleration measurement, which gives information with regard to a movement of the patient, and a sensor that detects the angular position of the rotor of the pump.

The rotary position sensor is necessary in particular with use of a magnetic bearing in order to determine the axial rotor position. This forms an important input variable for the control of the bearing and thus the magnetic mounting of the rotor. This is the case for example in INCOR pumps from Berlin Heart GmbH.

Figure 2:
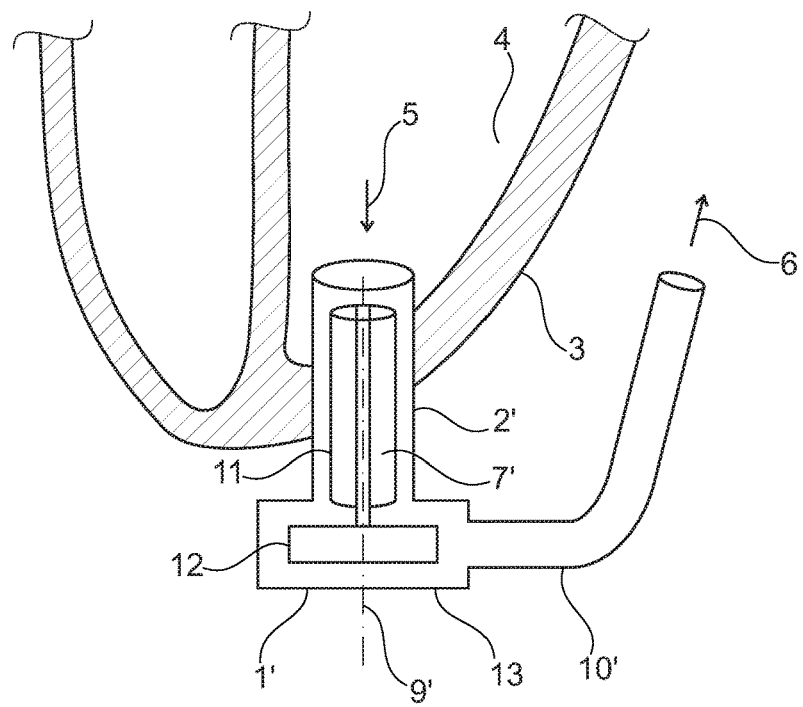
FIG. 2 shows a section through a heart wall with an implanted heart pump of a second design.

FIG. 2 shows a heart pump 1', of which the inlet connection piece 2' is also embedded in the heart wall 3 in the region of the left ventricle 4, wherein the axis of rotation 9' of the rotor 7' runs in the longitudinal direction of the inlet connection piece 2'. Here, the drive part 11 of the rotor with the armature and, as applicable, also a winding are housed in the inlet connection piece 2', whereas the rotor part with the conveying elements 12 is arranged in the pump housing 13. The rotor 12 accelerates the blood in the radial direction and partly in the tangential direction, so that it leaves the pump through the outlet connection piece 10'. A brushless electric motor can be used in this embodiment of the heart pump as well.

Figure 3:
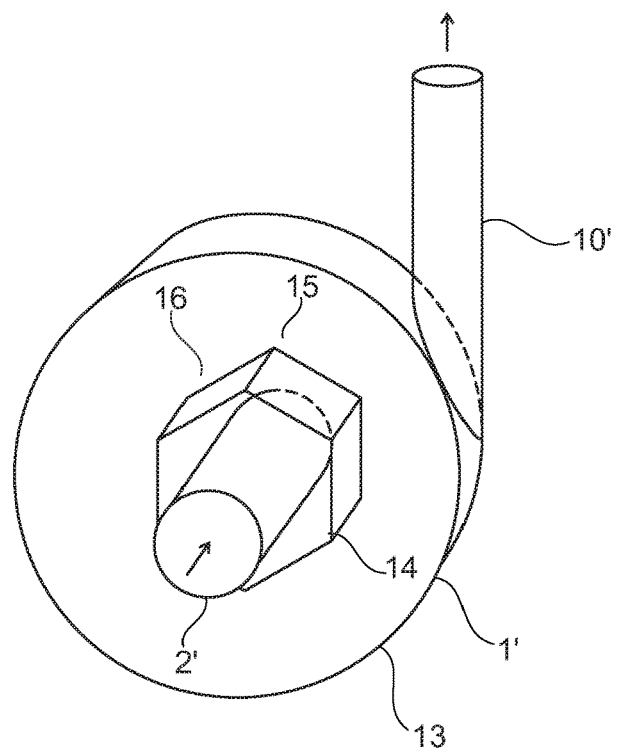
FIG. 3 shows a three-dimensional external view of a heart pump with a substantially polygonal annular printed circuit board surrounding an inlet connection piece of the pump.

FIG. 3 shows an external view of a heart pump 1' with an inlet connection piece 2' and an outlet connection piece 10' and a pump housing 13 in approximately cylindrical design, wherein a printed circuit board 14 folded in a polygonal manner is illustrated around the inlet connection piece 2' and carries electrical component parts of a signal processing device, although these are not illustrated in detail. FIG. 3 shows merely a space-saving arrangement of the signal processing device around the inlet connection piece 2' between the pump housing 13 and the heart wall 3. The printed circuit board 14 can have for example film hinge connections at the bending points 15, 16 between individual flat, planar printed circuit board parts, wherein conductor tracks of the printed circuit board can pass over the bending lines 15, 16.

Figure 4:
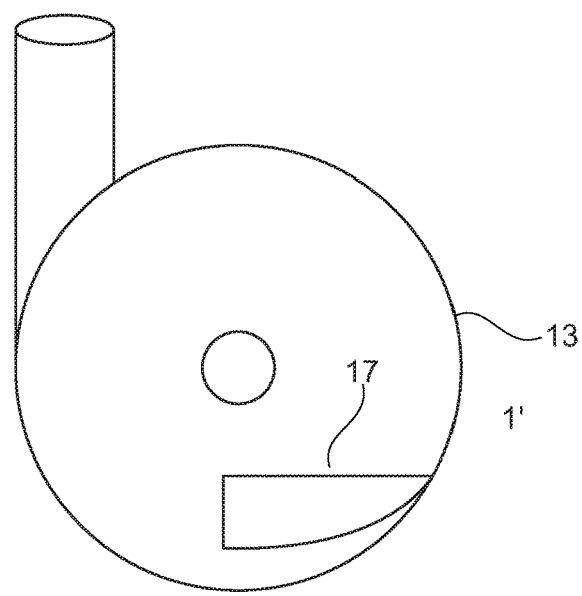
FIG. 4 shows a view of a base of a heart pump, in which a signal processing device is integrated.

FIG. 4 shows a view of a pump housing 13 as considered from the base of the pump, wherein an insert part 17 is installed in the base and can carry electrical components of a signal processing device. In this way as well, a signal processing device can be arranged on the heart pump 1' in a space-saving and directly protected manner.

Figure 5:
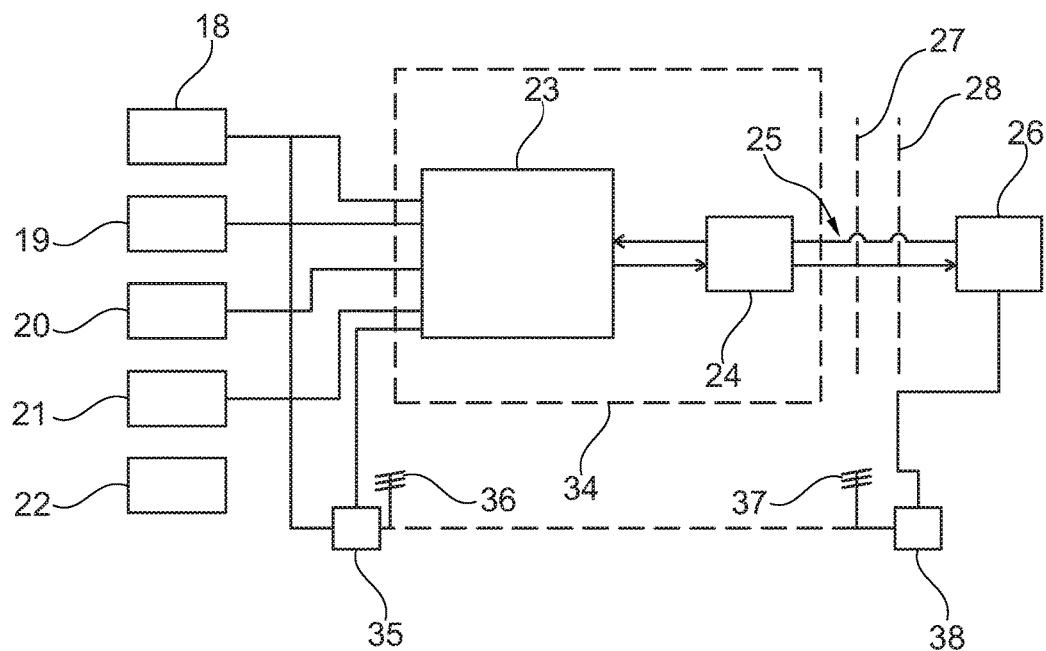
FIG. 5 shows the combining of the sensor data from different sensors in a signal processing device which is connected by means of a signal bus to a control device.

FIG. 5 shows in detail on the left side five sensors, specifically an electronic temperature sensor 18, an acceleration sensor 19, a blood temperature sensor 20, a ventricle pressure sensor 21, and a rotor position sensor 22, each of which is connected to a microcontroller 23. The microcontroller 23, together with a bus interface 24, forms a signal processing device 34, which communicates bidirectionally with a control device 26 via the transcutaneous or percutaneous line 25. Here, sensor measured values from the sensors 18, 19, 20, 21, 22 are transmitted via the transcutaneous bus line 25 to the control device 26, and signals can be conducted from the control device 26 to the heart pump, for example the drive of the heart pump. These include, for example, electrical signals for controlling the magnetic bearing. The transcutaneous line 25 can additionally be used for signal transmission and for the transmission of electrical energy.

The microcontroller 23 can combine the signals of the sensors or a selection of the sensors and can process these in such a way that they can be sent by means of a common communication protocol to the control device 26. As a result, the necessary line capacity of the transcutaneous line 25, for example the number of the required cores, can be reduced to a minimum, so that the transcutaneous line is thin and flexible and is thus less likely to break and in addition has a small outer surface and therefore offers a smaller interface to the tissue of the patient's body as potential attack area for infections.

The tissue layer through which the transcutaneous line 25 runs to outside the body, where the control device 26 is also arranged, is indicated by the two dashed lines 27, 28. In the case of a percutaneous line, this would lead for example to a TET interface arranged in the body, which can be coupled to a corresponding TET interface arranged outside the body. A control device could be arranged in the body, for example in the vicinity of the internally arranged TET interface and at a distance from the pump or pump electronics. Alternatively, the control device can also be arranged outside the body.

A radio link is provided parallel to the transcutaneous line 25, with an implanted transmitter 35, a transmitting antenna 36, a receiver 38, and a receiving antenna 37 outside the patient's body.

Figure 6:
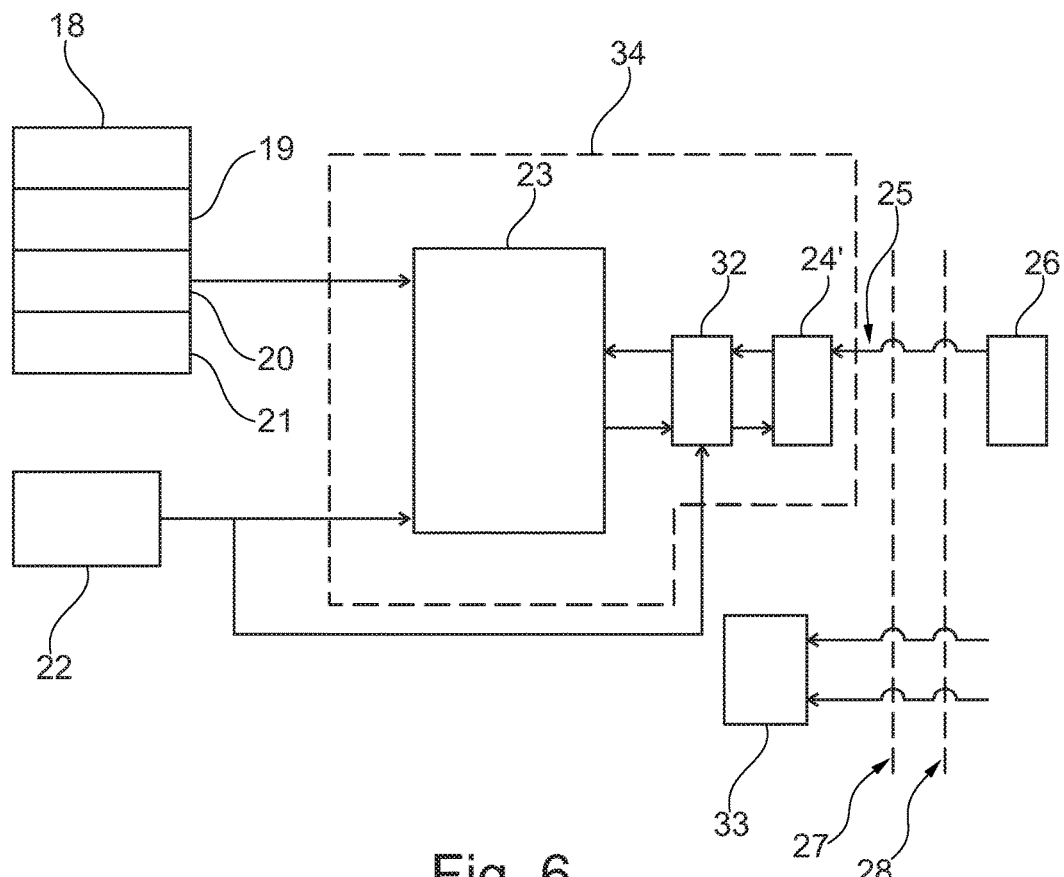
FIG. 6 shows a signal processing device which forwards the signal of a position sensor, at least in the event of a fault, with bypassing of key parts of the signal processing device via the transcutaneous line.

FIG. 6 shows that the microcontroller 23 can be bypassed by a bypass line 29 starting from the rotor position sensor 22. Whereas in the first operating state a multiplicity of sensor signals are processed by the signal processing device, the signal processing device for example digitalises the sensor signals or aggregates various signals, in the second operating state—for example in the case of a fault—the multiplicity of sensor signals or in some exemplary embodiments merely some of the sensor signals are transmitted via the bypass line 29, with bypassing of the microcontroller 23, to the control device arranged outside the body.

The sensor data from the sensors 18, 19, 20, 21, 22 is usually conducted to the microcontroller 23, processed there, and conducted from the microcontroller 23 for example via a RS485 transceiver 24' to the transcutaneous line 25, and via this to the external control device 26. The signal of the rotor position sensor 22 or a signal reflecting the position of the rotor can additionally be conducted by a low-pass filter, which is arranged upstream of the microcontroller.

In numerous exemplary embodiments, a monitoring device (for example a watchdog) is provided, which checks the correct functioning of the microcontroller 23. If a fault of the microcontroller 23 is signalled, the monitoring device by way of example can actuate a switch 32, which for example is an analogue switch and which transfers the heart pump device from a first operating state into a second operating state, in which the signal of the rotor position sensor 22, which reaches the switch via the bypass line 29, is connected through to the transceiver 24'. The signal of the rotor position sensor is thus conducted directly and without passing through the microcontroller, i.e. bypassing key parts of the signal processing device, to the transceiver 24' and the control device 26. It is thus ensured with a high level of certainty that the signals, for example the signals of the rotor position sensor, reach the control device 26 even in the event of a malfunction of the microcontroller, so that the drive of the heart pump can also be controlled properly under consideration of the rotor position. The control device 26 is for this purpose, and for the purpose of energy transfer, connected either via an additional line (not illustrated) or also via the transcutaneous line 25 to the motor drive of the heart pump motor.

In addition, a transcutaneous connection from outside the body to an implanted voltage supply 33 is also illustrated in FIG. 6. The transcutaneous connection, however, can alternatively also be percutaneous. In the case of a percutaneous line, the above-mentioned connection can also be percutaneous or transcutaneous.

As a result of the invention, the transcutaneous line 25 can thus be selected with minimal cores and a small surface, wherein at the same time a high functional reliability of the heart pump and a reliable controllability are ensured.

The invention claimed is:

1. A heart pump device comprising:
   an implantable heart pump, which includes at least one sensor, wherein the at least one sensor includes at least one of a position sensor for a rotor of the implantable heart pump, a position and/or acceleration sensor, a volume flow rate sensor, a temperature sensor, a pressure sensor, a pressure difference sensor, an oxygen saturation sensor, or a chemical sensor for blood analysis; and
   a control device, which is connected to the implantable heart pump by a transcutaneous line or a percutaneous line, wherein a signal processing device, which is configured to communicate via the transcutaneous line or the percutaneous line with the control device, and which is connected to the at least one sensor of the implantable heart pump, is configured to process, in a first operating state, a plurality of signals of the at least one sensor and is further configured to transmit the signals to the control device, and wherein a switching module is provided within the signal processing device, wherein the switching module is configured to transmit, in response to a fault of the signal processing device, the signals of the at least one sensor in a second operating state directly via the transcutaneous line, with bypassing of key parts of the signal processing device.

2. The heart pump device according to claim 1, wherein the signal processing device is arranged directly on the implantable heart pump.

3. The heart pump device according to claim 1, wherein a transmitting device is provided in an immediate vicinity of the implantable heart pump, in particular is directly connected thereto, and processes signals of the at least one sensor and transmits these by means of a wireless connection.

4. The heart pump device according to claim 1, wherein the signal processing device has at least one memory device for storing system parameters and/or measured values of one or more sensors.

5. The heart pump device according to claim 1, wherein the signal processing device has a microcontroller.

6. The heart pump device according to claim 1, wherein the signal processing device has a transceiver for a digital bus communication.

7. The heart pump device according to claim 1, wherein a supply voltage is conducted via the transcutaneous line or the percutaneous line.

8. The heart pump device according to claim 1, wherein the signal processing device has at least one flexible, in particular bendable or foldable printed circuit board.

9. The heart pump device according to claim 1, wherein the signal processing device is arranged annularly around an inflow or outflow channel of the implantable heart pump.

10. The heart pump device according to claim 1, wherein the signal processing device is arranged on a flat housing base of the implantable heart pump.

11. A method comprising:
    detecting a plurality of pump parameters in a signal processing device of a heart pump device, the heart pump device further comprising an implantable heart pump that includes at least one sensor, wherein the at least one sensor includes at least one of a position sensor for a rotor of the implantable heart pump, a position and/or acceleration sensor, a volume flow rate sensor, a volume flow rate sensor, a temperature sensor, a pressure sensor, a pressure difference sensor, an oxygen saturation sensor, or a chemical sensor for blood analysis; and
    storing the pump parameters in the signal processing device, wherein the implantable heart pump is configured to be controlled by a control device,
    wherein the signal processing device is configured to communicate with the control device via at least one of a transcutaneous line or a percutaneous line, wherein the signal processing device is configured to connect to the at least one sensor of the implantable heart pump, wherein the signal processing device is configured to process a plurality of signals of the at least one sensor and to transmit the signals of the at least one sensor to the control device via the at least one of the transcutaneous line or the percutaneous line, and wherein a switching module included in the signal processing device is configured to transmit, in response to a fault of the signal processing device, the signals of the at least one sensor in a second operating state directly via the transcutaneous line, with bypassing of key parts of the signal processing device.

12. The method according to claim 11 further comprising processing, by the signal processing device, the signals of the at least one sensor; and forwarding the signals via a databus.

13. A system comprising:

an implantable heart pump comprising at least one sensor, wherein the at least one sensor includes at least one of a position sensor for a rotor of the implantable heart pump, a position and/or acceleration sensor, a volume flow rate sensor, a volume flow rate sensor, a temperature sensor, a pressure sensor, a pressure difference sensor, an oxygen saturation sensor, or a chemical sensor for blood analysis; and a signal processing device, wherein the implantable heart pump is configured to be controlled by a control device, wherein the signal processing device is configured to communicate with the control device via at least one of a transcutaneous line or a percutaneous line, wherein the signal processing device is configured to connect to the at least one sensor of the implantable heart pump, wherein the signal processing device is configured to process a plurality of signals of the at least one sensor and to transmit the signals of the at least one sensor to the control device via the at least one of the transcutaneous line or the percutaneous line, and wherein a switching module is provided within the signal processing device, wherein the switching module is configured to transmit, in response to a fault of the signal processing device, the signals of the at least one sensor in a second operating state directly via the transcutaneous line, with bypassing of key parts of the signal processing device.

* * * * *